(12) United States Patent
Chono et al.

(10) Patent No.: US 9,822,380 B2
(45) Date of Patent: Nov. 21, 2017

(54) NUCLEIC ACID FOR TREATMENT OR PREVENTION OF IMMUNODEFICIENCY VIRUS INFECTION

(71) Applicant: TAKARA BIO INC., Shiga (JP)

(72) Inventors: Hideto Chono, Otsu (JP); Kazuya Matsumoto, Otsu (JP); Junichi Mineno, Otsu (JP); Ikunoshin Kato, Otsu (JP)

(73) Assignee: TAKARA BIO INC., Shiga (JP)

( * ) Notice: Subject to any disclaimer, the term of this patent is extended or adjusted under 35 U.S.C. 154(b) by 358 days.

(21) Appl. No.: 14/515,817

(22) Filed: Oct. 16, 2014

(65) Prior Publication Data

US 2015/0037300 A1    Feb. 5, 2015

Related U.S. Application Data

(62) Division of application No. 12/064,185, filed as application No. PCT/JP2006/315842 on Aug. 10, 2006, now Pat. No. 8,889,844.

(30) Foreign Application Priority Data

Aug. 16, 2005 (JP) ................................. 2005-236160
May 19, 2006 (JP) ................................. 2006-140243

(51) Int. Cl.
| | |
|---|---|
| *C12N 15/86* | (2006.01) |
| *C12N 5/0783* | (2010.01) |
| *C12N 9/22* | (2006.01) |
| *C12N 15/85* | (2006.01) |
| *A61K 31/7088* | (2006.01) |
| *C07K 14/47* | (2006.01) |
| *A61K 35/17* | (2015.01) |
| *A61K 38/46* | (2006.01) |
| *A61K 48/00* | (2006.01) |
| *A61K 38/00* | (2006.01) |

(52) U.S. Cl.
CPC .......... *C12N 15/86* (2013.01); *A61K 31/7088* (2013.01); *A61K 35/17* (2013.01); *A61K 38/465* (2013.01); *C07K 14/4702* (2013.01); *C12N 5/0636* (2013.01); *C12N 9/22* (2013.01); *C12N 15/85* (2013.01); *A61K 38/00* (2013.01); *A61K 48/00* (2013.01); *C12N 2510/00* (2013.01); *C12N 2830/002* (2013.01)

(58) Field of Classification Search
CPC .... A61K 38/00; A61K 48/00; A61K 31/7088; A61K 35/17; A61K 38/465; A61K 48/005; C12N 15/86; C12N 9/22; C12N 15/85; C12N 2510/00; C12N 2830/002; C12N 5/0636; C12N 2740/16043; C07K 14/4702

See application file for complete search history.

(56) References Cited

U.S. PATENT DOCUMENTS

| | | | |
|---|---|---|---|
| 5,554,528 A | 9/1996 | Harrison et al. | |
| 5,837,510 A | * 11/1998 | Goldsmith | ............. A61K 31/70 424/93.2 |
| 2010/0137415 A1 | 6/2010 | Chono et al. | ............... 514/44 R |

FOREIGN PATENT DOCUMENTS

| | | |
|---|---|---|
| EP | 0 454 781 B1 | 11/1991 |
| WO | 2004/113498 A2 | 12/2004 |
| WO | WO/2004/113498 | * 12/2004 |

OTHER PUBLICATIONS

Ragheb et al. Human Gene Therapy, 1999, 10, 103-112.*
Habu et al (Nucleic Acids Research, 2005, vol. 33, No. 1 235-243.*
Pleyer et al. (Progress in Retinal and Eye Research 22 (2003) 277-293.*
Ecke et al., Goodman & Gilman's The Pharmacological basis of Therapeutics, McGraw-Hill, New York, NY. 1996, pp. 77-101.*
Kay et al Nature Review, 2011, 12, 316-328.*
Thomas et al. Nature Rev. Genet. 4: 346-358; 2003).*
Verma et al Annu Rev Biochem. 2005;74:711-38.*
Chono et al , Human gene Therapy, 2011, 22, 35-43.*
Munoz-Gomez et al FEBS letter 2004, 567, 316-320.
Japanese Patent Office, Office Action dated Dec. 6, 2011 in Application No. 2007-530970.
Chono, et al., "Acquisition of HIV-1 resistance in T lymphocytes using an ACA-specific E. coli mRNA interface", *Hum Gene Ther.*, vol. 22(1), pp. 35-43, 2011.
Chono, et al., Abstract Only, "Acquisition of HIV-1 resistance in T lymphocytes using an ACA-specific E. coli mRNA interfase", *Hum Gene Ther.*, vol. 22(1), pp. 35-43, 2011.
Muñoz-Gómez, et al., "Rnase/Anti-RNase Activities of the Bacterial parD Toxin-Antitoxin System", *Journal of Bateriology*, vol. 187, No. 9, 3151-3157, May 2005.
Shimazu, et al., "NBK/BIK antagonizes MCL-1 and BCL-$X_L$ and activates BAK-mediated apoptosis in response to protein synthesis inhibition", *Genes & Development*, vol. 21, pp. 929-941, 2007.
Korean Patent Office, Office Action dated Mar. 29, 2011 in Application No. 10-2008-7006020.

(Continued)

*Primary Examiner* — Anoop Singh
(74) *Attorney, Agent, or Firm* — Browdy and Neimark, P.L.L.C.

(57) ABSTRACT

A nucleic acid comprising a transcription regulation sequence whose transcription is induced by a trans-acting factor of a human immunodeficiency virus and a gene encoding a polypeptide having an endoribonuclease activity specific to single-stranded RNA, wherein the gene is located in such a position that the expression of the gene can be regulated by the transcription regulation sequence; a method for production of a cell showing an inhibited replication of a human immunodeficiency virus therein, the method comprising the step of introducing the nucleic acid into a cell; and a method for treatment or prevention of a human immunodeficiency virus infection.

6 Claims, 2 Drawing Sheets

(56) References Cited

OTHER PUBLICATIONS

Munoz-Gomez, et al., "Insights into the specificity of RNA cleavage by the *Escherichia coil* MazF toxin", FEBS Letters, vol. 567, pp. 316-320, 2004.
Australian Patent Office, Written Opinion, dated Apr. 6, 2009, and established for Singapore Application No. SG 200801251-0.
European Patent Office, Extended European Search Report, dated Oct. 2, 2009 in Application No. 06796333.
Intellectual Property Office of Singapore, Examination Report, established Dec. 7, 2009 and dated Jan. 11, 2010 in Singapore Application No. SG 200801251-0.
Chinese Patent Office, Office Action, dated Feb. 12, 2010 in Chinese Patent Application No. 200680030024.5.
Hnatyszyn et al Gene Therapy 2001, 8, 1863-1871.
Chono et al.,"Development of anti-HIV gene therapy strategy using novel endoribonuclease, MazF (I)," Journal of Gene Medicine, 2006, pp. 1464-1465, vol. 8, No. 12.
Mineno et al.,"Development of anti-HIV gene therapy strategy using novel endoribonuclease, MazF (II)," Journal of Gene Medicine, 2006, pp. 1465, vol. 8, No. 12.
H. J. M. Brady et al. "Specific ablation of human immunodeficiency virus Tat-expressing cells by conditionally toxic retroviruses", Proc. Natl. Acad. Sci. USA, vol. 91, pp. 365-369, Jan. 1994.
Y. Habu et al., "Inhibition of HIV-1 gene expression by retroviral vector-mediated small-guide RNAs that direct specific RNA cleavage by tRNase ZL", Nucleic Acids Research, vol. 33, No. 1, pp. 235-243, 2005.
G. S. Harrison et al., "Activation of a Diphtheria Toxin A Gene by Expression of Human Immunodeficiency Virus-1 Tat and Rev Proteins in Transfected Cells", Human Gene Therapy, vol. 2, pp. 53-60, 1991.
P. A. Leland et al., "Ribonuclease A variants with potent cytotoxic activity", Proc. Natl. Acad. Sci. USA, vol. 95, pp. 10407-10412, Sep. 1998.
J. A. Ragheb et al., "Inhibition of Human Immunodeficiency Virus Type 1 by Tat/Rev-Regulated Expression of Cytosine Deaminase, Interferon a2, or Diphtheria Toxin Compared with Inhibition by Transdominant Rev", Human Gene Therapy, vol. 10, pp. 103-112, Jan. 1, 1999.
J. Zhang et al., "Interference of mRNA Function by Sequence-specific Endoribonuclease PemK", Journal of Biological Chemistry, vol. 279, No. 20, pp. 20678-20684, May 14, 2004.
Y. Zhang et al., "MazF Cleaves Cellular mRNAs Specifically at ACA to Block Protein Synthesis in *Escherichia coli*", Molecular Cell, vol. 12, pp. 913-923, Oct. 2003.
PCT International Preliminary Report on Patentability dated Feb. 28, 2008.

\* cited by examiner

```
                         SEQUENCE LISTING

<160> NUMBER OF SEQ ID NOS: 24

<210> SEQ ID NO 1
<211> LENGTH: 111
<212> TYPE: PRT
<213> ORGANISM: Escherichia coli

<400> SEQUENCE: 1

Met Val Ser Arg Tyr Val Pro Asp Met Gly Asp Leu Ile Trp Val Asp
1               5                   10                  15

Phe Asp Pro Thr Lys Gly Ser Glu Gln Ala Gly His Arg Pro Ala Val
            20                  25                  30

Val Leu Ser Pro Phe Met Tyr Asn Asn Lys Thr Gly Met Cys Leu Cys
        35                  40                  45

Val Pro Cys Thr Thr Gln Ser Lys Gly Tyr Pro Phe Glu Val Val Leu
    50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
            100                 105                 110

<210> SEQ ID NO 2
<211> LENGTH: 336
<212> TYPE: DNA
<213> ORGANISM: Escherichia coli

<400> SEQUENCE: 2
atggtaagcc gatacgtacc cgatatgggc gatctgattt gggttgattt tgacccgaca      60
aaaggtagcg agcaagctgg acatcgtcca gctgttgtcc tgagtccttt catgtacaac     120
aacaaaacag gtatgtgtct gtgtgttcct tgtacaacgc aatcaaaagg atatccgttc     180
gaagttgttt tatccggtca ggaacgtgat ggcgtagcgt tagctgatca ggtaaaaagt     240
atcgcctggc gggcaagagg agcaacgaag aaaggaacag ttgccccaga ggaattacaa     300
ctcattaaag ccaaaattaa cgtactgatt gggtag                              336

<210> SEQ ID NO 3
<211> LENGTH: 336
<212> TYPE: DNA
<213> ORGANISM: Artificial Sequence
<220> FEATURE:
<223> OTHER INFORMATION: Synthetic DNA encoding MazF.

<400> SEQUENCE: 3
atggtaagcc gatacgtacc cgatatgggc gatctgattt gggttgattt tgacccgacc      60
aaaggtagcg agcaagctgg ccatcgtcca gctgttgtcc tgagtccttt catgtataat     120
```

```
aataaaaccg gtatgtgtct gtgtgttcct tgtaccacgc aatcaaaagg atatccgttc    180
gaagttgttt tatccggtca ggaacgtgat ggcgtagcgt tagctgatca ggtaaaaagt    240
atcgcctggc gggcaagagg agcaacgaag aaaggaaccg ttgccccaga ggaactgcag    300
ctcattaaag ccaaaattaa cgtactgatt ggttaa                              336

<210> SEQ ID NO 4
<211> LENGTH: 30
<212> TYPE: DNA
<213> ORGANISM: Artificial Sequence
<220> FEATURE:
<223> OTHER INFORMATION: Primer 5' HIV1 U3 to amplify a portion of HIV
      LTR.

<400> SEQUENCE: 4
acgcgtctgg aagggctaat ttggtcccaa                                     30

<210> SEQ ID NO 5
<211> LENGTH: 36
<212> TYPE: DNA
<213> ORGANISM: Artificial Sequence
<220> FEATURE:
<223> OTHER INFORMATION: Primer 3'fHIV1 R to amplify a portion of HIV
      LTR.

<400> SEQUENCE: 5
gggcccggat cctgagcact caaggcaagc tttatt                              36

<210> SEQ ID NO 6
<211> LENGTH: 36
<212> TYPE: DNA
<213> ORGANISM: Artificial Sequence
<220> FEATURE:
<223> OTHER INFORMATION: Primer 3'fHIV1 TAR to amplify a portion of HIV
      LTR.

<400> SEQUENCE: 6
gggcccggat ccgggttccc tagttagcca gagagc                              36

<210> SEQ ID NO 7
<211> LENGTH: 30
<212> TYPE: DNA
<213> ORGANISM: Artificial Sequence
<220> FEATURE:
<223> OTHER INFORMATION: Primer 5'fMazF to amplify a DNA encoding MazF.

<400> SEQUENCE: 7
ggatccatgg taagccgata cgtacccgat                                     30

<210> SEQ ID NO 8
<211> LENGTH: 30
<212> TYPE: DNA
<213> ORGANISM: Artificial Sequence
<220> FEATURE:
<223> OTHER INFORMATION: Primer 3'fMazF to amplify a DNA encoding MazF.

<400> SEQUENCE: 8
agatctttaa ccaatcagta cgttaatttt                                     30

<210> SEQ ID NO 9
<211> LENGTH: 18
<212> TYPE: DNA
<213> ORGANISM: Artificial Sequence
<220> FEATURE:
<223> OTHER INFORMATION: Primer 5'fKpnI to amplify a DNA encoding GaLV
```

-continued envelope.

<400> SEQUENCE: 9
ggtaccatgg tattgctg                                                 18

<210> SEQ ID NO 10
<211> LENGTH: 19
<212> TYPE: DNA
<213> ORGANISM: Artificial Sequence
<220> FEATURE:
<223> OTHER INFORMATION: Primer 3' ClaI to amplify a DNA encoding GalV
      envelope.

<400> SEQUENCE: 10
atcgattgat gatgcatgg                                                19

<210> SEQ ID NO 11
<211> LENGTH: 33
<212> TYPE: DNA
<213> ORGANISM: Artificial
<220> FEATURE:
<223> OTHER INFORMATION: PCR primer NE1181-F to amplify a DNA encoding
      NE1181 polypeptide.

<400> SEQUENCE: 11
ggggagctaa catatgactg atttcaagca gcg                                33

<210> SEQ ID NO 12
<211> LENGTH: 36
<212> TYPE: DNA
<213> ORGANISM: Artificial
<220> FEATURE:
<223> OTHER INFORMATION: PCR primer NE1181-R to amplify a DNA encoding
      NE1181 polypeptide.

<400> SEQUENCE: 12
ggggctcgag caaatcaaag atgatcatta aagctg                             36

<210> SEQ ID NO 13
<211> LENGTH: 339
<212> TYPE: DNA
<213> ORGANISM: Nitrosomonas europaea ATCC 19718

<400> SEQUENCE: 13
atgactgatt tcaagcagcg ggatatttac tggatcgatc ttgaaccgac aaagggtgcg    60
gaaacaagaa aattaaggcc atgtgtaatt attcaaagtg acctggttaa cgttcaatcc   120
agaacagtga tagttgcccc tttgctcctt cagcataaac cctggccatt tgcagtgaat   180
ctggagccca cagaaaaaaa tggtctggat aaggatcgtc atatcaacct caagcaatta   240
cgcgcggttg atatttcacg cattggaaaa aaacaaggca ggcttgaaaa tagatacaag   300
gatcctatca aagcagcttt aatgatcatc tttgatttg                         339

<210> SEQ ID NO 14
<211> LENGTH: 113
<212> TYPE: PRT
<213> ORGANISM: Nitrosomonas europaea ATCC 19718

<400> SEQUENCE: 14

Met Thr Asp Phe Lys Gln Arg Asp Ile Tyr Trp Ile Asp Leu Glu Pro
1               5                   10                  15

Thr Lys Gly Ala Glu Thr Arg Lys Leu Arg Pro Cys Val Ile Ile Gln
            20                  25                  30

```
Ser Asp Leu Val Asn Val Gln Ser Arg Thr Val Ile Val Ala Pro Leu
         35                  40                  45

Leu Leu Gln His Lys Pro Trp Pro Phe Ala Val Asn Leu Glu Pro Thr
 50                  55                  60

Glu Lys Asn Gly Leu Asp Lys Asp Arg His Ile Asn Leu Lys Gln Leu
 65                  70                  75                  80

Arg Ala Val Asp Ile Ser Arg Ile Gly Lys Lys Gln Gly Arg Leu Glu
                 85                  90                  95

Asn Arg Tyr Lys Asp Pro Ile Lys Ala Ala Leu Met Ile Ile Phe Asp
            100                 105                 110

Leu

<210> SEQ ID NO 15
<211> LENGTH: 339
<212> TYPE: DNA
<213> ORGANISM: Artificial Sequence
<220> FEATURE:
<223> OTHER INFORMATION: Synthetic DNA encoding NE1181 polypeptide.

<400> SEQUENCE: 15
atgactgatt tcaagcagcg ggatatttac tggatcgatc ttgaaccgac aaagggtgcg      60
gaaacaagaa agttaaggcc atgtgtaatt attcaaagtg acctggttaa cgttcaatcc     120
agaacagtga tagttgcccc tttgctcctt cagcataaac cctggccatt tgcagtgaac     180
ctggagccca cagaaaaaaa cggtctggat aaggatcgtc atatcaacct caagcaatta     240
cgcgcggttg atatttcacg cattggaaaa aaacaaggca ggcttgaaaa cagatacaag     300
gatcctatca aagcagcttt aatgatcatc tttgatttg                            339

<210> SEQ ID NO 16
<211> LENGTH: 33
<212> TYPE: DNA
<213> ORGANISM: Artificial
<220> FEATURE:
<223> OTHER INFORMATION: PCR primer DR0662-F to amplify a DNA encoding
      DR0662 polypeptide.

<400> SEQUENCE: 16
ggggagctaa catatggctg taggactcat ccg                                   33

<210> SEQ ID NO 17
<211> LENGTH: 28
<212> TYPE: DNA
<213> ORGANISM: Artificial
<220> FEATURE:
<223> OTHER INFORMATION: PCR primer DR0662-R to amplify a DNA encoding
      DR0662 polypeptide.

<400> SEQUENCE: 17
ggggctcgag cagggcaagg tgaaggcg                                         28

<210> SEQ ID NO 18
<211> LENGTH: 345
<212> TYPE: DNA
<213> ORGANISM: Deinococcus radiodurans R1

<400> SEQUENCE: 18
atggctgtag gactcatccg gcgcggcgac attttttctga cccatttcgg ccccgcccgc     60
gcaggcgaac cggacttcaa cgccccgct gtggtcatca ccaacaatgt cgccaacgcc     120
aaagcggatg ccgtgaccgt cattccgctc accagcaacc tggaaaccct ctacgatttt    180
```

```
caactgctgc tccccaccga gcgaaccggg ctgaacttgg acagcaaagc gcagacggaa      240
ttgatctcgt gtattgccat cagccgcatc gggaagcacc tggggcaagt gccagccgac      300
ctcatggctg aactggacgc cagaatccgc cttcaccttg ccctg                      345
```

```
<210> SEQ ID NO 19
<211> LENGTH: 115
<212> TYPE: PRT
<213> ORGANISM: Deinococcus radiodurans R1

<400> SEQUENCE: 19

Met Ala Val Gly Leu Ile Arg Arg Gly Asp Ile Phe Leu Thr His Phe
1               5                   10                  15

Gly Pro Ala Arg Ala Gly Glu Pro Asp Phe Lys Arg Pro Ala Val Val
            20                  25                  30

Ile Thr Asn Asn Val Ala Asn Ala Lys Ala Asp Ala Val Thr Val Ile
        35                  40                  45

Pro Leu Thr Ser Asn Leu Glu Thr Leu Tyr Asp Phe Gln Leu Leu Leu
    50                  55                  60

Pro Thr Glu Arg Thr Gly Leu Asn Leu Asp Ser Lys Ala Gln Thr Glu
65                  70                  75                  80

Leu Ile Ser Cys Ile Ala Ile Ser Arg Ile Gly Lys His Leu Gly Gln
                85                  90                  95

Val Pro Ala Asp Leu Met Ala Glu Leu Asp Ala Arg Ile Arg Leu His
            100                 105                 110

Leu Ala Leu
        115
```

```
<210> SEQ ID NO 20
<211> LENGTH: 25
<212> TYPE: DNA
<213> ORGANISM: Artificial
<220> FEATURE:
<223> OTHER INFORMATION: PCR primer to amplify a DNA encoding DR0662
      polypeptide.

<400> SEQUENCE: 20
gggggatatc caccatggct gtagg                                            25
```

```
<210> SEQ ID NO 21
<211> LENGTH: 25
<212> TYPE: DNA
<213> ORGANISM: Artificial
<220> FEATURE:
<223> OTHER INFORMATION: PCR primer to amplify a DNA encoding DR0662
      polypeptide.

<400> SEQUENCE: 21
ggggtctaga ttacagggca aggtg                                            25
```

```
<210> SEQ ID NO 22
<211> LENGTH: 34
<212> TYPE: DNA
<213> ORGANISM: Artificial
<220> FEATURE:
<223> OTHER INFORMATION: PCR primer to amplify a DNA encoding MazF.

<400> SEQUENCE: 22
atatgagctc caccatggta agccgatacg tacc                                  34
```

```
<210> SEQ ID NO 23
<211> LENGTH: 33
```

```
<212> TYPE: DNA
<213> ORGANISM: Artificial
<220> FEATURE:
<223> OTHER INFORMATION: PCR primer to amplify a DNA encoding MazF.

<400> SEQUENCE: 23
atatgaattc tcattaacca atcagtacgt taa                                   33

<210> SEQ ID NO 24
<211> LENGTH: 249
<212> TYPE: DNA
<213> ORGANISM: Escherichia coli

<400> SEQUENCE: 24
atgatccaca gtagcgtaaa gcgttgggga aattcaccgg cggtgcggat cccggctacg      60
ttaatgcagg cgctcaatct gaatattgat gatgaagtga agattgacct ggtggatggc    120
aaattaatta ttgagccagt gcgtaaagag cccgtattta cgcttgctga actggtcaac    180
gacatcacgc cggaaaacct ccacgagaat atcgactggg gagagccgaa agataaggaa    240
gtctggtaa                                                            249
```

NUCLEIC ACID FOR TREATMENT OR PREVENTION OF IMMUNODEFICIENCY VIRUS INFECTION

TECHNICAL FIELD

The present invention relates to a nucleic acid construct that is useful for treatment or prevention of a disease caused by immunodeficiency virus infection.

BACKGROUND ART

Human immunodeficiency virus (HIV) infects a cell expressing a CD4 molecule (e.g., a T cell) to destroy the cell. Therefore, the number of CD4-positive T cells (helper T cells) is decreased and the cellular immunity is lowered in a human body infected with HIV. The infection finally leads to severe immunodeficiency conditions, resulting in onset of an opportunistic infection such as *carinii pneumonia*. The conditions are called acquired immunodeficiency syndrome (AIDS).

As to methods for treating HIV infection, antiviral agents that block the life cycle of the HIV (reverse transcriptase inhibitors, protease inhibitors, etc.) and vaccines have been developed, and several antiviral agents have been put to practical use. However, since the mutation frequency in the HIV is high, a mutant against which the above-mentioned agents are not effective may emerge in an infected individual. Thus, it cannot be necessarily said that a specific remedy has been completed. In another approach, attempts to develop gene therapy drugs using nucleic acids (an RNA decoy, a ribozyme, etc.) or proteins (transdominant mutant proteins, intracellular antibodies, etc.) as effective ingredients to inhibit the multiplication of HIV have not attained the stage of completion.

A method in which cell death is caused specifically in a cell infected with HIV has been devised (e.g., Patent Document 1, Non-patent Documents 1, 2 and 3). According to such a method, a gene encoding a product that exhibits cytotoxicity is connected downstream of an LTR promoter from HIV. To date, there has been no known case where the method is clinically applied. Use of a ribonuclease as the product that exhibits cytotoxicity is described in Patent Document 2 (U.S. Pat. No. 5,837,510), although death of HIV-infected cells caused by the ribonuclease has not been confirmed. It is known that human pancreatic ribonuclease (RNase 1), which is a representative ribonuclease, is inhibited by a ribonuclease inhibitor in cytoplasm (Non-patent Document 4). Thus, it cannot be said that it is suitable for the above-mentioned purpose.

It has been reported that several prokaryotic plasmids have a post-segregation killing (PSK) function to kill hosts from which the plasmids have been dropped out in order to maintain the plasmids in the hosts. Such plasmids have toxin-antitoxin genes. An antitoxin binds to a toxin in a cell to inactivate the toxin. The antitoxin is labile to degradation by proteases. Degradation of the antitoxin by proteases results in activation of the toxin which is stable. Such toxin-antitoxin genes also exist on chromosomes of most prokaryotes. They respond to various stresses and have functions in programmed cell death. Although the functions of the toxins have not been fully proven, it is known that both MazF, which is a toxin of the mazE-mazF system (Non-patent Document 5), and PemK, which is a toxin of the pemI-pemK system (Non-patent Document 6), have sequence-specific ribonuclease activities. Furthermore, a method for obtaining a highly pure protein of interest has been proposed (Patent Document 3). In this method, mRNA is degraded utilizing such a toxin, and only an mRNA encoding the protein of interest from which the sequences cleaved by the toxin have been eliminated beforehand is translated.

Patent Document 1: U.S. Pat. No. 5,554,528
Patent Document 2: U.S. Pat. No. 5,837,510
Patent Document 3: WO 2004/113498
Non-patent Document 1: Hum. Gene Therapy, 2: 53-61 (1991)
Non-patent Document 2: Proc. Natl. Acad. Sci. USA, 91:365-369 (1994)
Non-patent Document 3: Hum. Gene Therapy, 10:103-112 (1999)
Non-patent Document 4: Proc. Natl. Acad. Sci. USA, 95:10407-10412 (1998)
Non-patent Document 5: Molecular Cell, 12:913-920 (2003)
Non-patent Document 6: J. Biol. Chem., 279:20678-20684 (2004)

DISCLOSURE OF INVENTION

Problems to be Solved by the Invention

The present invention has been made in view of the above-mentioned prior art. The main object of the present invention is to provide a more highly effective method for treating an HIV infection.

Means to Solve the Problems

The present inventors have found that expression of a polypeptide having a single-stranded RNA-specific endoribonuclease activity is induced to degrade mRNA in a cell upon infection with HIV in the cell which has a transferred nucleic acid construct in which a gene encoding the polypeptide having a single-stranded RNA-specific endoribonuclease activity is connected downstream of a transcription regulation sequence with which transcription is induced by a trans activator of human immunodeficiency virus and, as a result, replication of the HIV in the cell and infection to other cells can be prevented. Thus, the present invention has been completed.

The present invention relates to:

[1] a nucleic acid comprising:
a transcription regulation sequence with which transcription is induced by a trans activator of human immunodeficiency virus; and
a gene encoding a polypeptide having a single-stranded RNA-specific endoribonuclease activity,
wherein the gene is placed so that its expression can be controlled by said sequence;

[2] the nucleic acid according to [1], which comprises a transcription regulation sequence with which transcription is induced by Tat protein and/or Rev protein;

[3] the nucleic acid according to [1], wherein the gene encoding a polypeptide having a single-stranded RNA-specific endoribonuclease activity is placed downstream of LTR of human immunodeficiency virus;

[4] the nucleic acid according to [1], wherein the polypeptide having a single-stranded RNA-specific endoribonuclease activity has an activity of cleaving an RNA in a nucleotide sequence-specific manner;

[5] the nucleic acid according to [1], wherein the polypeptide having a single-stranded RNA-specific endoribonuclease activity is MazF protein;

[6] the nucleic acid according to any one of [1] to [4], which is incorporated into a vector;

[7] a method for producing a cell in which replication of human immunodeficiency virus is suppressed, the method comprising transferring the nucleic acid defined by any one of [1] to [6] into a cell;

[8] the method according to [7], wherein the cell is a cell population containing a T cell or a T cell precursor;

[9] the method according to [7], wherein the nucleic acid is transferred into the cell using a virus vector;

[10] the method according to [9], wherein the nucleic acid is transferred into the cell using a retrovirus vector or an adenovirus vector;

[11] a method for treating or preventing human immunodeficiency virus infection, the method comprising transferring the nucleic acid defined by any one of [1] to [6] into a cell.

Effects of the Invention

The present invention provides a nucleic acid construct that enables suppression of replication of human immunodeficiency virus (HIV) in a cell. The nucleic acid construct is useful for treatment of HIV infection.

BEST MODE FOR CARRYING OUT THE INVENTION

Figure 1:
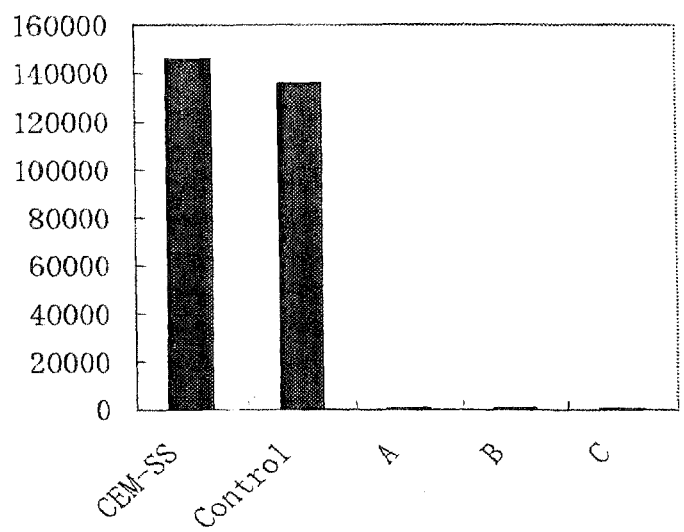
FIG. 1 illustrates amounts of HIV-derived proteins in culture supernatants of cells infected with HIV.

The nucleic acid construct of the present invention is composed of a transcription regulation sequence with which transcription is induced by a trans activator of human immunodeficiency virus; and a gene encoding a polypeptide having a single-stranded RNA-specific endoribonuclease activity, wherein the gene is placed so that its expression can be controlled by said sequence.

There is no specific limitation concerning the transcription regulation sequence with which transcription is induced by a trans activator of human immunodeficiency virus. For example, a transcription regulation sequence with which transcription is induced by Tat protein of HIV may be used. The Tat protein binds to TAR (trans-activation responsive element) sequence in an RNA of which the transcription is initiated by the action of LTR promoter of the HIV to activate transcription of a region downstream of the sequence. Thus, a transcription regulation sequence that has a nucleotide sequence of the TAR region downstream of the transcription initiation site can be used according to the present invention. In particular, LTR of HIV or a transcription regulation sequence obtained by subjecting LTR to an appropriate modification can be preferably used. Examples of the modifications include deletion of a binding site for a host cell-derived transcription factor in a promoter, and deletion of a region that is unnecessary for Tat-specific transcription. Using the former modification, it is possible to reduce the level of transcription by the host cell-derived transcription factor which is irrelevant to the HIV infection. For example, such a modification of a transcription regulation sequence is described in Non-patent Document 2. The latter modification is exemplified by deletion of U5 region or a region downstream of TAR sequence in LTR (a part of R region and the U5 region). The nucleic acid of the present invention that has such deleted LTR is advantageous to production of a high-titer retrovirus vector having the nucleic acid.

It is known that RRE (Rev-responsible element) in HIV genome interacts with an HIV-derived trans activator, Rev protein, to promote protein expression (Non-patent Document 3). It is known that a region called INS in gag and pol genes suppresses transcription of HIV mRNA in the absence of the Rev protein, but the suppressive action is canceled by the interaction between the RRE and the Rev protein (J. Virol., 66:7176-7182 (1992)). Thus, if such a transcription regulation sequence is incorporated at a position 3' to a foreign polypeptide-encoding gene in the nucleic acid of the present invention, it is possible to express the polypeptide encoded by the nucleic acid in a manner dependent on the Rev protein, i.e., on HIV infection.

The sequence that interact with an HIV-derived trans activator may be used in combination with a functional sequence with which the sequence is inherently incorporated (e.g., a promoter) or in combination with a heterologous functional sequence. For example, the "transcription regulation sequences" used according to the present invention include a sequence constructed by combining the sequence and a promoter that is not derived from HIV and that is capable of initiating mRNA transcription in a cell for which transfer of the nucleic acid of the present invention is desired.

The nucleic acid of the present invention is constructed by connecting a gene encoding a polypeptide having a single-stranded RNA-specific endoribonuclease activity to the above-mentioned transcription regulation sequence so that the expression of the gene can be controlled by the transcription regulation sequence.

As used herein, a single-stranded RNA-specific endoribonuclease activity means an activity of hydrolyzing a phosphodiester bond 3' to a ribonucleotide in a single-stranded nucleic acid containing at least one ribonucleotide molecule as a constituting nucleotide. A nucleic acid hydrolyzed with the above-mentioned activity generates the following: a 3' end having a hydroxyl group and a 5' end having a phosphate group; a 3' end having a phosphate group and a 5' end having a hydroxyl group; or a 5' end having 2',3'-cyclic phosphate and a hydroxyl group. Although it is not intended to limit the present invention, a polypeptide that cannot cleave double-stranded nucleic acids such as a double-stranded RNA or an RNA-DNA hybrid may be used according to the present invention. Such substrate specificity is suitable for the present invention in view of efficient degradation of an HIV genome which is single-stranded RNA. In particular, one having an activity of cleaving RNA in a nucleotide sequence-specific manner or capable of degrading mRNA in a ribosome-independent manner is preferably used according to the present invention. Examples of such polypeptides include enzymes called mRNA interferases such as MazF or PemK as described below (Patent Document 2).

Although it is not intended to limit the present invention, for example, the polypeptide having an activity of degrading a single-stranded RNA in a sequence-specific and ribosome-independent manner used according to the present invention may be derived from a microorganism. In this case, a gene encoding the polypeptide can be isolated from a microbial genome or a plasmid. For example, a gene encoding MazF or PemK, which is an endoribonuclease that constitutes a toxin of a toxin-antitoxin system as described in Non-patent Document 4 or 5, can be used according to the present invention. MazF is an enzyme that cleaves a sequence 5'-A/CA-3' in a single-stranded RNA, and PemK is an enzyme that mainly cleaves a sequence 5'-U/A(C, A or U)-3' in a single-stranded RNA. It is also possible to select a gene encoding an amino acid sequence highly homologous to the amino acid sequence of MazF or PemK from a known database and to isolate it for use according to the present invention. Polypeptides having such activities have been found in many microorganisms including blue-green algae and archaebacteria [*Bacillus subtilis* 168 (NP_388347; 5'-U/ACAU-3'), *Neisseria meningitidis* ATCC13090 (NP_275029; 5'-/ACU-3'), *Deinococcus radiodurans* R1 (NP_294385; 5'-UU/CCUUU-3'), *Micobacterium bovis* BCG (NP_855664; 5'-U/CCUU-3'), *Nostoc* sp. PCC7120 (NP_487251; 5'-U/ACA-3'), *Enterococcus faecalis* V583 (NP_816859; 5'-U/ACAU-3'), *Nitrosomonas europaea* ATCC19718 (NP_841355; 5'-GA/AU-3', 5'-G/AAU-3', 5'-AA/AU-3' or 5'-A/AAU-3'), *Pyrococcus horikoshii* ATCC700860 (NP_143082; 5'-U/GG-3', 5'-U/UG-3', 5'-U/GA-3', 5'-A/GG-3' or 5'-A/AG-3'): accession nos. of polypeptides having the activities in NCBI Protein Database, and the nucleotide sequences recognized and cleaved by the polypeptides are indicated in parentheses]. Preferably, a gene encoding MazF is used according to the present invention. The amino acid sequence of MazF and a nucleotide sequence of a gene encoding MazF are shown in SEQ ID NOS. 1 and 2, respectively.

Since the endoribonuclease that constitutes a toxin of a toxin-antitoxin system is not inhibited by a cytoplasmic ribonuclease inhibitor such as human placental ribonuclease inhibitor (Patent Document 3), it is suitable for use according to the present invention. If the endoribonuclease is persistently expressed, de novo protein synthesis does not take place in the cell, resulting in inhibition of cell growth and induction of cell death. However, since the enzyme does not degrade rRNA constituting ribosome or tRNA forming a higher order structure, the ability of the cell to grow can be restored once the HIV RNA is degraded and eliminated, and expression of the endonuclease is terminated in the cell into which the nucleic acid of the present invention is transferred. Thus, even if HIV is integrated as a provirus into a chromosome in a cell, the cell in which the replication of the virus is prevented retains its ability to grow. The use of the above-mentioned endoribonuclease is advantageous in that replication of an HIV and onset of AIDS can be prevented without greatly reducing the number of T cells in a living body.

An endoribonuclease that constitutes a toxin of a toxin-antitoxin system recognizes a short nucleotide sequence (about 3 to 7 nucleotides) to cleave a single-stranded RNA. Therefore, if the endoribonuclease is expressed in a cell, most of the mRNAs in the cell are degraded and protein synthesis in the cell and growth of the cell are inhibited. Furthermore, since the RNA as the HIV genome is also cleaved, replication of the HIV and release (budding) of the HIV out of the cell are also prevented. In addition, since expression of polypeptides encoded in the HIV genome is also inhibited, for example, induction of apoptosis in a cell not infected with the HIV due to an extracellularly released Tat protein is suppressed as well.

For treating or preventing HIV infection, it is desirable to transfer the nucleic acid construct of the present invention into cells (or a cell population) containing a cell that can be infected with HIV, that is, a CD4-positive cell. Thus, gene transfer is carried out according to the present invention targeting a CD4-positive cell (e.g., a T cell), a precursor cell that is capable of differentiating into a CD4-positive cell (e.g., a hematopoietic stem cell), or a cell population containing such a cell. It is preferable to target a hematopoietic stem cell or a cell population containing said cell according to the present invention in view of comprehensive transfer of the nucleic acid construct into cells that can be infected with an HIV. There is no specific limitation concerning the cells as long as they contain a CD4-positive cell or a precursor cell thereof. Examples of cells include blood cells (peripheral blood cells, umbilical cord blood cells) or bone marrow cells collected from an individual, as well as CD4-positive cells, precursor cells of CD4-positive cells and hematopoietic stem cells fractionated from said cells according to a known method.

There is no specific limitation concerning the method for transferring the nucleic acid construct of the present invention into a cell. For example, the nucleic acid of the present invention may be incorporated into a plasmid vector or a virus vector and transferred into a cell using an appropriate method. If a plasmid vector is to be used, a gene transfer method such as a phosphate calcium method, a cationic lipid method, a liposome method or an electroporation method may be used. If the nucleic acid is to be incorporated into a virus vector (e.g., a retrovirus vector, an adenovirus vector, an adeno-associated virus vector or a herpes virus vector), the cell of interest may be infected under conditions suitable for the virus to transfer the nucleic acid of the present invention. A retrovirus vector which is capable of integrating the nucleic acid of the present invention into a chromosome is preferable according to the present invention.

In an embodiment in which a retrovirus is used, there is no specific limitation concerning the retrovirus vector to be used according to the present invention. According to the present invention, a replication-defective retrovirus vector is preferable for preventing unlimited infection or gene transfer. Such a vector is made replication-defective so that it cannot autonomously replicate in an infected cell and therefore avirulent. Such a vector can invade a host cell such as a vertebrate cell (in particular, a mammalian cell) to stably integrate a foreign gene, which is inserted into the vector, into the chromosomal DNA. Examples of known replication-defective retrovirus vectors include retrovirus vectors (e.g., MFG vector, α-SGC vector (WO 92/07943), pBabe (Nucleic Acids Research, 18:3587-3596 (1990)), pLXIN (Clontech) or pDON-AI (Takara Bio)), lentivirus vectors and modifications thereof. Examples of the lentivirus vectors include, but are not limited to, human immunodeficiency virus (HIV)-derived vectors (an HIV vector having a wild-type LTR (e.g., U.S. Pat. No. 5,665,577) or an HIV vector having a modified LTR (e.g., pLenti6/V5, Invitrogen)) and simian immunodeficiency virus (SIV)-derived vectors (e.g., Human Gene Therapy, 11:1863-1874 (2000)).

The retrovirus vector may be prepared according to a known method and used according to the present invention. There is no specific limitation concerning the preparation method. A culture supernatant collected from a culture of a retrovirus producer cell suitable for the retrovirus vector to be used can be used according to the present invention. The retrovirus producer cell may be either one that stably produces retrovirus particles in the supernatant or one that transiently produces retrovirus particles upon transfection with a retrovirus vector plasmid.

A known packaging cell line such as PG13 (ATCC CRL-10686), PA317 (ATCC CRL-9078), GP+E-86 or GP+envAm-12 (U.S. Pat. No. 5,278,056), or Psi-Crip (Proc. Natl. Acad. Sci. USA, 85:6460-6464 (1988)) may be used for preparing a retrovirus producer cell. 293 cell or 293T cell of which the transfection efficiency is high may be used for preparing a retrovirus producer cell.

According to the present invention, it is also possible to use a retrovirus prepared by pseudotyped packaging which has an envelope derived from a virus different from the one from which the genome of the retrovirus vector is derived. For example, a pseudotyped retrovirus having an envelope derived from Moloney murine leukemia virus (MoMLV), gibbon ape leukemia virus (GaLV), vesicular stomatitis virus (VSV) or feline endogenous virus, or a protein that can function as an envelope can be used. Furthermore, one may use according to the present invention a retrovirus vector having on its surface a protein that is subjected to sugar chain modification. The retrovirus vector may be prepared using a retrovirus producer cell having a transferred gene for an enzyme involved in glycosylation or the like.

According to the present invention, a transcription regulation sequence with which transcription is induced by a trans activator of a human immunodeficiency virus, and a gene encoding a polypeptide having a single-stranded RNA-specific endoribonuclease activity placed downstream of the transcription regulation sequence are inserted into one of the above-mentioned various vectors (preferably, the above-mentioned retrovirus vectors). Furthermore, a sequence that regulates the transcription of the gene (an operator, an enhancer, a terminator, etc.) may be included. Furthermore, the nucleic acid of the present invention may have, independent of the gene, an appropriate marker gene which enables selection of a cell having a transferred gene (e.g., a drug resistance gene, a gene encoding a fluorescent protein, or a gene encoding an enzyme that can function as a reporter such as β-galactosidase or luciferase), a receptor gene or the like. In addition, the nucleic acid of the present invention may be loaded with a suicide gene in order to eliminate cells having the transferred gene from the living body in cases where the treatment with the cells having the transferred gene is completed or any side effect is caused.

In one embodiment of the present invention, ex vivo gene transfer in which a vector is transferred into a cell collected from a biological individual outside the living body is used. If a virus vector is to be used, gene transfer is achieved by mixing the target cells collected from a living body with a virus vector (e.g., a culture supernatant of a virus producer cell or a virus vector purified from such a culture supernatant) and incubating the mixture under appropriate conditions. If a vector that can be used to transfer a gene in vivo (e.g., an adenovirus vector) is to be used, the vector containing the nucleic acid of the present invention may be administered directly into an individual.

If a retrovirus vector is to be used for ex vivo gene transfer, it is possible to infect a target cell with the retrovirus vector with high efficiency in the presence of a functional substance having a retrovirus-binding activity.

For example, methods of gene transfer using a functional substance having a retrovirus-binding activity are described in WO 95/26200, WO 97/18318 and Nature Medicine, 2:876-882 (1996). The methods include a method in which a functional substance having both a retrovirus-binding site and a target cell-binding site in a single molecule is used, and a method in which a mixture of a functional substance having a retrovirus-binding site and a functional substance having a target cell-binding site is used. Both methods can be used according to the present invention.

There is no specific limitation concerning the functional substance as long as it has a retrovirus-binding activity and/or a target cell-binding activity. For example, the functional substance having a retrovirus-binding activity is exemplified by a heparin-binding domain from fibronectin (heparin-II domain), fibroblast growth factor, a fragment of type V collagen, a derivative or a variant of such a polypeptide, polylysine, DEAE-dextran or the like. Any substance capable of binding to the target cell of interest can be used as a functional substance having a target cell-binding activity. Although it is not intended to limit the present invention, for example, the functional substance having a target cell-binding activity is exemplified by a polypeptide having a cell-binding activity (e.g., a cytoskeletal protein), an antibody that recognizes a cell or a biological molecule on a cell surface, a growth factor, a cytokine or a sugar chain.

A method in which a gene is transferred into a target cell in the presence of a functional substance comprising a heparin-binding domain from fibronectin exemplifies one preferable embodiment of the present invention. A preferable example of the functional substance is a fibronectin fragment having both a cell adhesion domain and a heparin-binding domain. In particular, a polypeptide of a region of binding to VLA-5 and/or VLA-4 is preferably used as the cell adhesion domain. Such a fibronectin fragment can be prepared from fibronectin purified from a living body using a means such as digestion with a protease, or produced using recombinant DNA techniques. For example, the recombinant fibronectin fragment commercially available from Takara Bio under the name of RetroNectin (registered trademark) is preferable according to the present invention.

As described above, the present invention is useful for production of a cell composition that is useful for treatment or prevention of human immunodeficiency virus infection. Furthermore, the present invention provides a method for treating or preventing HIV infection using the cell composition. Administration, into an individual, of cells having the nucleic acid of the present invention being transferred enables reduction in HIV-infected cells in the individual or suppression of HIV replication in the cells.

If a CD4-positive cell having the nucleic acid of the present invention being transferred, or a CD4-positive cell differentiated from a precursor cell of a CD4-positive cell (e.g., a hematopoietic stem cell) having the nucleic acid of the present invention being transferred, is infected with an HIV and an HIV-derived trans activator is generated in the cell, expression of a gene encoding a polypeptide having a single-stranded RNA-specific endoribonuclease activity placed downstream of a transcription regulation sequence is induced, mRNA in the cell is degraded by the generated polypeptide, and protein biosynthesis is inhibited. At the same time, an RNA genome which is generated in the course of HIV replication is also degraded. Since translation of polypeptides encoded by the HIV genome and replication of the HIV genome are inhibited as described above, de novo production of infectious HIV particles and infection of other cells are prevented.

The activity of an endoribonuclease that constitutes a toxin of a toxin-antitoxin system (e.g., MazF or PemK) is suppressed by the coexistence of the corresponding antitoxin (e.g., MazE or PemI). Thus, if a gene for an endoribonuclease which is a toxin is to be used according to the present invention, exertion of cytotoxicity due to the endoribonuclease activity in cells not infected with an HIV can be suppressed or controlled by using an antitoxin gene in combination. In one exemplary embodiment, the activity of a toxin may be suppressed by the action of an antitoxin by expressing, in cells not infected with HIV, a trace amount of the antitoxin from a gene for the antitoxin connected downstream of a promoter for an appropriate housekeeping gene (e.g., glyceraldehyde 3-phosphate dehydrogenase gene, R-actin gene). If such a cell is infected with HIV, expression of the toxin is promoted by the action of the trans activator, and the cytotoxicity is exhibited only after the amount of expressed toxin exceeds the amount of expressed antitoxin. Thus, it is possible to further increase the selectivity of cytotoxicity to HIV-infected cells.

According to a previously reported method in which HIV-infected cells are destroyed by the action of a cytotoxic protein (e.g., diphtheria toxin) or an enzyme that activates a nontoxic precursor into a cytotoxic compound (e.g., thymidine kinase), the toxin released from destroyed cells or the activated compound may enter into cells not infected with HIV to exhibit cytotoxicity. On the other hand, the possibility of damaging the surrounding cells is low according to the method of the present invention in which a polypeptide having a single-stranded RNA-specific endoribonuclease activity is used.

Multiple drug combination therapy in which 3 or 4 antiviral agents (reverse transcriptase inhibitors, protease inhibitors, etc.) are used in combination (HAART) is currently the mainstream of HIV infection treatment methods. Such therapy remarkably decreases the HIV amount in blood of a patient infected with the HIV, resulting in amelioration of clinical symptoms. However, it is difficult to completely eliminate HIV due to the existence of HIV-infected cells that do not actively produce virus particles (long-term survival infected cells; reservoirs). The present invention may be carried out in combination with HAART.

A polypeptide having an endoribonuclease activity is expressed in response to expression of Tat in a cell having the nucleic acid construct of the present invention being transferred. If the nucleic acid construct is present in a cell in which HIV is integrated into a chromosome as a provirus, transcription of RNA from the provirus is initiated, expression of a polypeptide having an endoribonuclease activity is induced by Tat which is transcribed from the RNA, and single-stranded RNA in the cell (including the HIV genome) is degraded. As a result, replication and budding of the HIV are inhibited in such a cell. When the HIV-derived RNA is degraded to terminate the Tat expression and Tat expressed prior to the termination disappears in the cell, expression of the polypeptide having an endoribonuclease activity is also terminated. Since ribosome or tRNA in a cell is not destroyed according to the present invention in which a polypeptide having an endoribonuclease activity that specifically acts on single-stranded RNA is used (Non-patent Document 5), normal protein synthesis is resumed once the expression of the polypeptide is terminated, and growth of cells that have not been destroyed at this time point is resumed.

EXAMPLES

The following Examples illustrate the present invention in more detail, but are not to be construed to limit the scope thereof.

Example 1: Construction of Tat Expression Plasmid

A region encoding Tat and sgGFP was removed from a plasmid pQBI-tatGFP (Quantum Biotechnologies Inc.) by double digestion with SacII and EcoRI, and a Tat-encoding sequence to which an initiation codon and a termination codon had been attached on the 5' side and 3' side, respectively, was inserted into the plasmid. The plasmid constructed as described above was designated as pQBI-TAT. The plasmid is a plasmid that can be used to express the Tat protein under the control of CMV promoter/enhancer.

Example 2: Construction of MazF Expression Plasmid

A region encoding gag, sgGFP and RRE was removed from a plasmid pQBI-LTRgagGFP (Quantum Biotechnologies Inc.) by double digestion with restriction enzymes SalI and XbaI, and a chemically synthesized DNA encoding MazF protein (SEQ ID NO:3) was inserted into the plasmid. The plasmid constructed as described above was designated as pQBI-LTRMazFcv1.

The plasmid is a plasmid that can be used to express the MazF protein under the control of the HIV 5'LTR. The nucleotide sequence of SEQ ID NO:3 encodes the amino acid sequence of MazF (SEQ ID NO:1). In the nucleotide sequence, ACA nucleotide sequences present in the MazF gene are replaced by other nucleotide sequences without altering the naturally-occurring MazF amino acid sequence. Since the RNA for MazF transcribed from this plasmid is not cleaved with the MazF activity, it can stably express MazF in a cell.

Example 3: Transfer of Plasmid into Cell $1 \times 10^5$ of human 293T/17 cells (ATCC CRL-11268) were added to each well of a 24-well collagen-coated plate and cultured for 24 hours. Dulbecco's modified Eagle medium (DMEM, Sigma) containing 10% fetal calf serum (Gibco) was used as a medium. 0.25 g of pQBI-LTRMazFcv1 or 0.25 µg each of pQBI-LTRMazFcv1 and pQBI-TAT was then transferred into cells in each well. TransIT-293 (Mirus) was used for the plasmid transfer and the procedure followed the attached instructions. The procedure was carried out in duplicate for each group. A group into which 0.25 µg each of pQBI-LTRgagGFP (Quantum Biotechnologies Inc.), which does not comprise MazF gene, and pQBI-TAT was transferred was used as a control.

The cells into which the plasmid(s) had been transfected were cultured at 37° C. with 5% $CO_2$ for 48 hours. The cells were observed under a microscope after cultivation. In the control group into which pQBI-LTRgagGFP and pQBI-TAT had been transfected, expression of the GFP protein by simultaneous transfer of pQBI-LTRgagGFP and pQBI-TAT was confirmed. Thus, it was confirmed that the promoter activity of the LTR was induced in a TAT-dependent manner. In wells with transfer of pQBI-LTRMazFcv1 alone, no difference was recognized as compared with the control. In the group with simultaneous transfer of pQBI-LTRMazF and pQBI-TAT, suppression of cell growth was clearly recognized as compared with the control. This shows that expression of MazF from pQBI-LTRMazF was dependent from the Tat protein. Thus, it was suggested that the construct in which MazF gene is placed under the control of the Tat protein-inducible LTR could be used to suppress the growth of cells infected with an HIV.

Example 4: Construction of Retrovirus Vector Plasmid (1) Construction of MazF Expression Retrovirus Vector Plasmid pSIN-HLTR-MazF The plasmid pQBI-LTRMazFcv1 constructed in Example 1 was cleaved with restriction enzymes StuI and XbaI to obtain an expression cassette of about 1340 bp that expresses MazF under the control of HIV-LTR, which was blunted using DNA Blunting Kit (Takara Bio).

For eliminating the LTR promoter activity in a retrovirus vector plasmid pDON-AI (Takara Bio), a portion from the NheI site to the SacI site in the U3 region of the 3'LTR was deleted and the plasmid was reconstructed to obtain a self-inactivating retrovirus vector plasmid pSIN which lost the LTR promoter activity. pSIN was cleaved at the PmeI site and dephosphorylated using Alkaline Phosphatase *E. coli* C75 (Takara Bio), and the expression cassette was inserted thereinto using DNA ligation kit Mighty Mix (Takara Bio). The plasmid constructed as described above was designated as pSIN-HLTR-MazF.

(2) Construction of MazF Expression Retrovirus Vector Plasmids pMTD3-U3R-MazF and pMTD3-U3TAR-MazF A plasmid vector pMTD3 was constructed by deleting a portion from the 43rd nucleotide to the 309th nucleotide in the 3'LTR U3 region of a vector pMT (Gene Therapy, 11:94-99 (2004)). A U3-R region and a U3-TAR region of HIV to be used as internal promoters were obtained by PCR using the plasmid pSIN-HLTR-MazF constructed in Example 4-(1) as a template. The nucleotide sequences of the primers used for amplifying the U3-R region, 5'HIV1 U3 and 3'HIV1 R are shown in SEQ ID NOS:4 and 5, respectively. A combination of 5'HIV U3 and a primer 3' HIV1 TAR (SEQ ID NO:6) was used for amplifying the U3-TAR region. Each of the PCR-amplified fragments was digested with MluI and BamHI and inserted between MluI and BamHI sites in pMTD to construct two retrovirus vector plasmids pMTD3-U3R and pMTD3-U3TAR.

A gene encoding MazF was obtained by PCR using the plasmid pSIN-HLTR-MazF as a template. The nucleotide sequences of the two primers used for amplification, 5'MazF and 3'MazF, are shown in SEQ ID NOS:7 and 8, respectively. The resulting amplified fragment was digested with BglII and BamHI, and inserted into the BamHI site in pMTD3-U3R or pMTD3-TAR. MazF expression retrovirus vector plasmids constructed as described above were designated as pMTD3-U3R-MazF and pMTD3-U3TAR-MazF, respectively.

(3) Construction of Control Retrovirus Vector Plasmid

An expression plasmid having a gene encoding a fluorescent protein eGFP being inserted into pMTD3-U3R was constructed for use as a control. Specifically, a DNA fragment comprising eGFP gene excised from a plasmid pGemT-Easy-eGFP (J. Gene Med., 6:724-733 (2004)) by digestion with BamHI and BglII was inserted into the BamHI site in pMTD3-U3R or pMTD3-TAR to construct two retrovirus vector plasmids pMTD3-U3R-GFP and pMTD3-U3TAR-GFP as eGFP expression plasmids.

Example 5: Establishment of MazF-Expressing CEM-SS Cell Line (1) An envelope expression plasmid to be used for preparing GaLV pseudotyped virus was constructed as follows. First, a DNA fragment encoding a GaLV virus envelope protein was amplified by PCR using genomic DNA prepared from PG13 cells (ATCC CRL-10686) as a template. The nucleotide sequences of two primers used for amplification, 5'KpnI and 3'ClaI, are shown in SEQ ID NOS:9 and 10, respectively. An amphotropic envelope expression plasmid pVM-AE (Gene Therapy, 10:706-711 (2003)) was digested with KpnI and ClaI to prepare a plasmid fragment from which envelope protein-encoding regions except a portion for the R peptide had been eliminated. The above-mentioned amplified fragment was digested with KpnI and ClaI, and inserted into the plasmid fragment to obtain a GaLV envelope expression plasmid pVM-GeR.

(2) $2 \times 10^6$ 293 T cells were placed in a 6-cm plate containing DMEM supplemented with 10% fetal bovine serum (FBS). Transfection was carried out by a calcium phosphate method using 4 µg of the retrovirus vector plasmid (one of the plasmids constructed in Example 4), 4 µg of a packaging plasmid pVM-GP (Gene Therapy, 10:706-711 (2003)) and the GaLV envelope expression plasmid pVM-GeR. The medium was exchanged for a fresh one 6 hours after initiation of transfection, and the cultivation was continued. The culture supernatant was collected after two days and filtrated through a 0.45-µm filter, and the filtrate was used as a virus supernatant in subsequent experiments.

CEM-SS cells were cultured in RPMI 1640 (Life Technologies) supplemented with 10% FBS at 37° C. in the presence of 5% $CO_2$. 1 ml of one of the retrovirus vectors (virus supernatants) prepared in Example 6-(1) and polybrene at a final concentration of 8 µg/ml were added to $5 \times 10^5$ CEM-SS cells in 2 ml of the medium in each well of a 6-well cell culture plate. The plate was centrifuged using a CR322 centrifuge (Jouan) at 25° C. at 2800 rpm for 99 minutes to promote adsorption of the retrovirus vector to the cells. After centrifugation, the cells were incubated at 37° C. in the presence of 5% $CO_2$ for 2 hours. The cells were then transferred into T25 flasks, and the cultivation was continued at 37° C. in the presence of 5% $CO_2$. After two days, cells having a transferred gene were selected using geneticin (G418) at 1 mg/ml to produce polyclonal cell lines transformed with the respective viruses.

Figure 2:
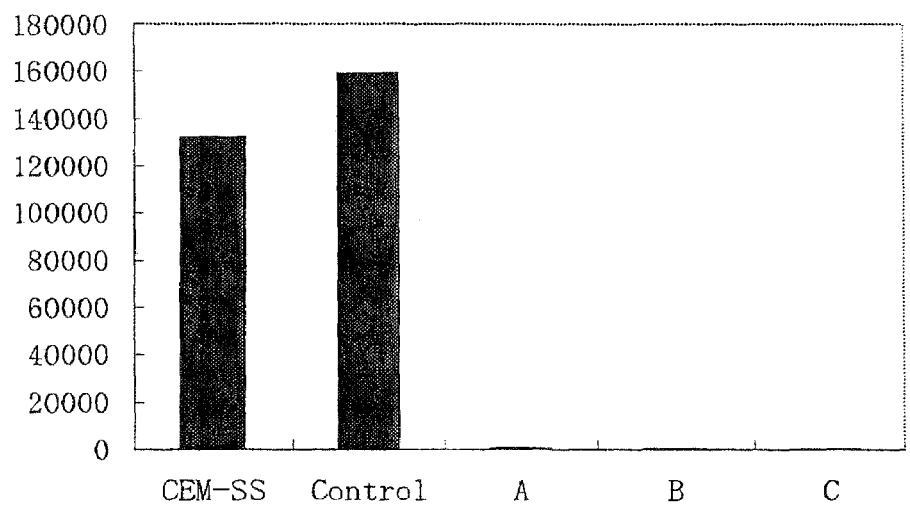
FIG. 2 illustrates amounts of HIV-derived proteins in culture supernatants of cells infected with HIV.
Figure 3:
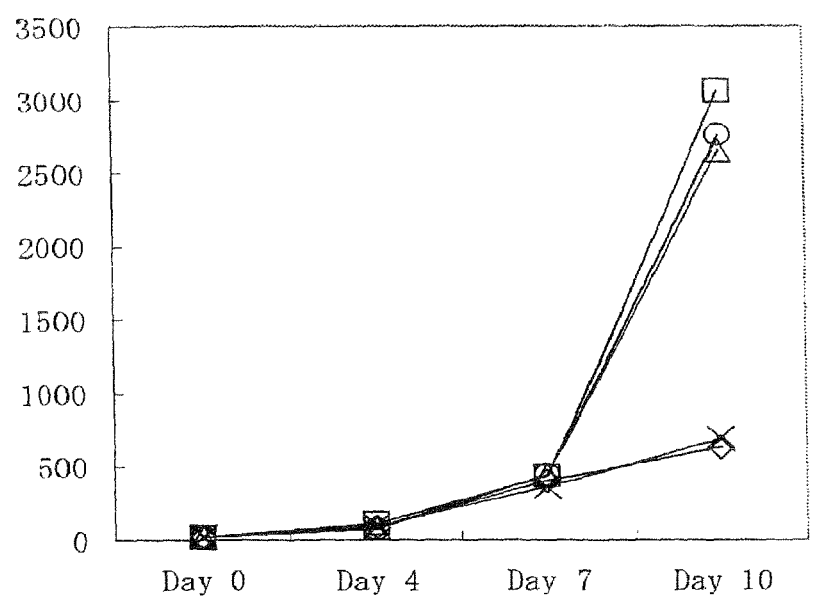
FIG. 3 illustrates time course of viable cell numbers in cultures of cells infected with HIV.

Example 6: HIV Infection $2 \times 10^6$ of one of the cell lines produced in Example 5 in 1 ml of the medium in each well of a 24-well cell culture plate were inoculated with a varying amount of HIV-1 IIIb (corresponding to 0.2, 2, 20 or 200 ng of the p24 protein), and the cells were cultured at 37° C. for 2 hours. The cells were washed in PBS and suspended in 10 ml of RPMI supplemented with 10% FBS and transferred into a T25 flask. Portions of the culture supernatant were collected from the flask over time, and amounts of p24 were quantified using an ELISA method (p24 ELISA kit, PerkinElmer) to estimate the HIV amounts. Experimental results are shown in FIGS. 1 and 2. FIGS. 1 and 2 illustrate results obtained seven and ten days after infection, respectively. In the figures, CEM-SS represents the results for CEM-SS cells without a transferred gene, Control represents the results for cells transformed with pMTD3-U3R-GFP virus, and A, B and C represent results for cells transformed with pSIN-HLTR-MazF, pMTD3-U3R-MazF virus and pMTD3-U3TAR-MazF virus, respectively. The longitudinal axis represents the amount of the p24 protein in ng/ml. Furthermore, viable cell numbers were counted on Day 4, Day 7 or Day 10 after infection using a trypan blue exclusion test. The results are shown in FIG. 3. In FIG. 3, diamond represents the results for CEM-SS cells without a transferred gene, x represents the results for cells transformed with pMTD3-U3R-GFP virus, and square, triangle and circle represent results for cells transformed with pSIN-HLTR-MazF, pMTD3-U3R-MazF virus and pMTD3-U3TAR-MazF virus, respectively. The longitudinal axis represents the viable cell number ($10^4$).

As shown in FIGS. 1 and 2, it was shown that the HIV amount in the culture supernatant of the cells transformed with the retrovirus containing the MazF gene was very low as compared with the CEM-SS cells without a transferred gene or the cells transformed with pMTD3-U3R-GFP virus without the MazF gene which was used as a control. Furthermore, comparison of growth rates for cells in the respective groups as shown in FIG. 3 shows that growth rate of cells transformed with the retrovirus containing the MazF gene was increased seven days after infection. This suggests that cell death caused by the HIV was suppressed in these cells. In addition, cells transformed with pSIN-HLTR-MazF, pMTD3-U3R-MazF virus or pMTD3-U3TAR-MazF virus were infected with the HIV and the cultivation was continued for 60 days. Although the HIV was not detected in the culture supernatants, HIV-derived DNAs were detected in DNAs extracted from the cells. Thus, it was shown that the HIV was retained in the cells as a provirus. This suggests that the cells transformed with the nucleic acid of the present invention were growing after infection with the HIV while replication and budding of the HIV were prevented.

Furthermore, similar infection tests were carried out except that the amount of inoculated HIV was increased up to an amount corresponding to 1000 ng of p24, and the amounts of p24 in culture supernatants were measured 16 days after infection. Also in this case, the amount of p24 in a culture supernatant of cells transformed with each retrovirus vector having MazF gene was ¹⁄₁₀₀₀ or less of the amount observed for the nontransformed cells or the control cells.

Example 7: Cell Growth Inhibition by Expression of Various mRNA Interferases in Tat-Dependent Manner (1) Isolation of NE1181 gene from *N. europaea* ATCC19718 and construction of retrovirus vector plasmid An amino acid sequence of a polypeptide encoded in *Nitrosomonas europaea* ATCC19718-derived NE1181 gene as well as the nucleotide sequence therefor were obtained from NCBI database (accession nos. NP_841237 and NC_004757). A primer NE1181-F (SEQ ID NO:11) and a primer NE1181-R (SEQ ID NO:12) were synthesized for PCR amplification of a DNA region encoding the entire polypeptide based on the information about the nucleotide sequence of NE1181.

*Nitrosomonas europaea* ATCC19718 genomic DNA was obtained from ATCC (ATCC No. 19718D).

PCR was conducted using Pyrobest DNA polymerase (Takara Bio) as well as 50 ng of the genomic DNA from *Nitrosomonas europaea* ATCC19718 and the primers NE1181-F and NE1181-R to obtain a 362-bp amplified DNA fragment. The amplified fragment was digested with restriction enzymes NdeI and XhoI and subjected to agarose gel electrophoresis, and a 341-bp DNA fragment was recovered from the gel. A recombinant plasmid was obtained by ligating the 341-bp DNA fragment to a vector pET21a (Novagen) which had been digested with restriction enzymes NdeI and XhoI. This recombinant plasmid was used to transform *Escherichia coli* JM109. A plasmid was prepared from a colony of a transformant obtained as described above and the nucleotide sequence was confirmed. Then, the plasmid was designated as an expression vector pET-NE1181.

The nucleotide sequence encoding the *Nitrosomonas europaea* ATCC19718-derived NE1181 polypeptide inserted into the expression vector pET-NE1181 and the amino acid sequence of the polypeptide are shown in SEQ ID NOS:13 and 14, respectively. In the polypeptide expressed using the expression vector pET-NE1181, a histidine tag that consists of eight amino acid residues including six histidine residues is attached at the C terminus of the polypeptide of the amino acid sequence of SEQ ID NO:1. It was confirmed using synthetic oligoribonucleotides as substrates that the polypeptide transcribed from NE1181 recognizes a 4-nucleotide sequence GAAU or AAAU to cleave RNA.

Since NE1181 gene has recognition sequences cleaved by NE1181 polypeptide itself in the mRNA, a gene with mutated codons was artificially synthesized so that such recognition sequences were eliminated and the encoded amino acid sequence was not altered. The nucleotide sequence of the gene is shown in SEQ ID NO:15. The artificially synthesized NE1181 gene was inserted into the BamHI site in the retrovirus vector plasmid pMTD3-U3TAR constructed in Example 4. The NE1181 expression retrovirus vector plasmid constructed as described above was designated as pMTD3-U3TAR-N4.

(2) Isolation of DR0662 from *Deinococcus Radiodurans* R1 and Construction of Retrovirus Vector Plasmid Isolation of DR0662 from *D. radioduran* R1 and Mb2014c homolog from *M. bovis* BCG, and construction of expression plasmids The amino acid sequence and the nucleotide sequence for *Deinococcus radioduran* R1-derived DR0662 were obtained from NCBI database (accession nos. NP_294385 and NC_001263). A primer DR0662-F (SEQ ID NO:16) and a primer DR0062-R (SEQ ID NO:17) were synthesized for PCR amplification of a DNA region encoding the entire polypeptide based on the information about the nucleotide sequence of DR0662.

*Deinococcus radioduran* R1 genomic DNA was obtained from ATCC (ATCC No. 13939D). PCR was conducted using Pyrobest DNA polymerase (Takara Bio) as well as 50 ng of the genomic DNA from *Deinococcus radioduran* R1 and the primers DR0662-F and DR0662-R to obtain a 368-bp amplified DNA fragment. The amplified fragment was digested with restriction enzymes NdeI and XhoI and subjected to agarose gel electrophoresis, and a 347-bp DNA fragment was recovered from the gel. A recombinant plasmid was obtained by ligating the 347-bp DNA fragment to a vector pET21a (Novagen) which had been digested with restriction enzymes NdeI and XhoI. The recombinant plasmid was used to transform *Escherichia coli* JM109. The plasmid was prepared from a colony of a transformant obtained as described above and the nucleotide sequence was confirmed. Then, the plasmid was designated as an expression vector pET-DR0662.

The nucleotide sequence encoding the *Deinococcus radioduran* R1-derived DR0662 polypeptide inserted into the thus obtained expression vector pET-DR0662 and the amino acid sequence of the polypeptide are shown in SEQ ID NOS:18 and 19, respectively. In the polypeptide expressed using the expression vectors pET-DR0662 and pET-Mb2014HIg, a histidine tag that consists of eight amino acid residues including six histidine residues is attached at the C terminus of the polypeptide of SEQ ID NO:1. It was confirmed using synthetic oligoribonucleotides as substrates that the polypeptide transcribed from DR0662 recognizes a 7-nucleotide sequence UUCCUUU to cleave RNA.

DR0662 gene obtained by PCR using pET-DR0662 as a template was inserted into the BamHI site in the retrovirus vector plasmid pMTD3-U3TAR constructed in Example 4. The DR0662 expression retrovirus vector plasmid constructed as described above was designated as pMTD3-U3TAR-D3. Primers used for amplifying the DR0662 gene are shown in SEQ ID NOS:20 and 21.

(3) Construction of Tat Expression Retrovirus Vector pQBI-Tat as described in Example 1 was digested with restriction enzymes SacII and EcoRV, blunted and inserted into the PmeI site in the retrovirus vector plasmid pDON-AI to construct pDON-Tat. pDON-Tat was digested with BamHI and XhoI to eliminate the SV40 promoter and the neomycin phosphotransferase gene. An IRES-ZsGreen gene fragment was obtained from pIRES2-ZsGreen1 (Clontech) and inserted downstream of the Tat gene in pDON-Tat digested with the restriction enzymes to construct pDON-Tat-ZsGreen.

G3T-hi cells (Takara Bio) were placed in a 6-cm plate containing DMEM supplemented with 10% fetal bovine serum (FBS). Transfection was carried out by a calcium phosphate method using 10 μg of the retrovirus vector plasmid pDON-Tat-ZsGreen and Retrovirus Packaging Kit Ampho (Takara Bio). The medium was exchanged for a fresh one 8 hours after initiation of transfection, and the cultivation was continued. The medium was exchanged again 24 hours after initiation of transfection. After 24 hours, the culture supernatant was collected and filtrated through a 0.45-μm filter, and the filtrate was used as a virus supernatant in subsequent experiments. A Tat protein and a green fluorescent protein ZsGreen are expressed from a cell having this virus being transferred.

(4) Establishment of CEM Cell Lines Having Transferred Gene Encoding MazF, NE1181 or DR0662

G3T-hi cells (Takara Bio) were placed in a 6-cm plate containing DMEM supplemented with 10% fetal bovine serum (FBS). Transfection was carried out by a calcium phosphate method using 10 μg of the retrovirus vector plasmid (either pMTD3-U3TAR-MazF, pMTD3-U3TAR-N4 or pMTD3-U3TAR-D3) and Retrovirus Packaging Kit Ampho (Takara Bio). The medium was exchanged for a fresh one 8 hours after initiation of transfection, and the cultivation was continued. The medium was exchanged again 24 hours after initiation of transfection. After 24 hours, the culture supernatant was collected and filtrated through a 0.45-μm filter, and the filtrate was used as a virus supernatant in subsequent experiments.

CEM cells were cultured in RPMI-1640 supplemented with 10% FBS at 37° C. in the presence of 5% $CO_2$. A 24-well non-tissue culture-treated plate was coated with RetroNectin (Takara Bio) according to the protocol. 0.5 ml of one of the above-mentioned virus supernatants was added to the well. The plate was centrifuged at 32° C. at 2000×g for 2 hours to adsorb the retrovirus vector to the RetroNectin-coated plate. After the supernatant was removed, 1 ml of a CEM cell suspension at $1 \times 10^5$ cells/ml was added thereto and the plate was incubated at 37° C. in the presence of 5% $CO_2$ for 24 hours. Cells having a transferred gene were cultured in a medium containing geneticin (G418) at 1 mg/ml for three weeks to produce polyclonal cell lines transformed with the respective viruses.

(5) Inhibition of Cell Growth by Induction of Expression of MazF, NE1181 and DR0662

(1) A 24-well non-tissue culture-treated plate was coated with RetroNectin (Takara Bio) according to the protocol. 0.5 ml of the Tat expression retrovirus vector prepared in Example 8 was added to the well. The plate was centrifuged at 32° C. at 2000×g for 2 hours to adsorb the retrovirus vector to the RetroNectin-coated plate. After the supernatant was removed, 1 ml of a suspension of one of the CEM cell lines expressing MazF, NE1181 or DR0662 prepared in Example 9 at $1 \times 10^5$ cells/ml was added to the well for infection. CEM cell without a transferred mRNA interferase gene was used as a control and subjected to infection with the Tat expression retrovirus vector in a similar manner. Efficiency of infection with Tat expression retrovirus was determined by measuring the ratio of ZsGreen-positive cells using a flow cytometer 2 or 15 days after infection. The results are shown in Table 1. As shown in Table 1, the gene was expressed in a Tat protein-dependent manner in CEM cells having a transferred mRNA interferase gene encoding MazF, NE1181 or DR0662, resulting in induction of cell death associated with mRNA degradation and decrease in ZsGreen-positive cell ratio. Based on the above-mentioned results, it was shown that growth of cells infected with the HIV could be suppressed also in cases where genes for mRNA interferases having nucleotide sequence specificities different from that of MazF were used.

TABLE 1

|  | ZsGreen-positive cell ratio (Tat virus-positive cell ratio) (%) | |
| --- | --- | --- |
|  | Day 2 | Day 15 |
| CEM with transferred MazF | 6.64 | 1.38 |
| CEM with transferred NE1181 | 28.62 | 15.96 |
| CEM with transferred DR0662 | 49.51 | 13.70 |
| CEM | 54.31 | 43.42 |

Example 8: mRNA Degradation by MazF Expression and Analysis of Ribosomal RNA (1) A vector with which MazF and a fluorescent protein ZsGreen are expressed from a single mRNA was constructed as follows. A MazF gene was obtained by PCR using pQBI-LTRMazFcv1 as described in Example 2 as a template, and the PCR-amplified MazF gene was inserted between SacI and BamHI sites in pIRES2-ZsGreen1 (Clontech). The constructed plasmid with which MazF and ZsGreen are simultaneously expressed was designated as pMazF-IZ. Primers used for amplifying the MazF gene are shown in SEQ ID NOS:22 and 23. A plasmid pLuc-IZ in which a luciferase gene was inserted between SacI and BamHI sites in pIRES2-ZsGreen1 was constructed as a control.

(2) Human 293 cells (ATCC CRL-1573) were cultured in DMEM medium supplemented with 10% fetal bovine serum (FBS). 0.5 ml of a suspension of 293 cells at $2 \times 10^5$ cells/ml was seeded into each well of a 24-well collagen-coated plate (Corning) and the cells were cultured for 24 hours. Transfection of pMazF-IZ or pLuc-IZ was carried out using TransIT-293 (Mirus). Expression of the fluorescent protein was analyzed using a flow cytometer FACS Vantage (Becton Dickinson) after 24, 48 or 72 hours. Total RNA was recovered using RNeasy micro (Qiagen). The recovered RNA was analyzed using micro electrophoresis apparatus Agilent 2100 Bioanalyzer (Agilent). Fluorescence intensity values from cells subjected to gene transfer determined by the flow cytometric analysis are shown in Table 2. As shown in Table 2, it was shown that expression of ZsGreen was suppressed in cells having pMazF-IZ being transferred. It is considered that this was due to degradation of mRNA by the action of expressed MazF which resulted in suppressed translation of ZsGreen. Ratios of 28s ribosomal RNA to 18s ribosomal RNA determined by electrophoresis analysis of total RNAs are shown in Table 3. As shown in Table 3, the ratios of 28s ribosomal RNA to 18s ribosomal RNA observed for cells having pMazF-IZ being transferred and cells having pLuc-IZ being transferred were equivalent to each other. Thus, it was shown that ribosomal RNA was not degraded by expression of MazF.

TABLE 2

| | ZsGreen fluorescence intensity | | |
| --- | --- | --- | --- |
| | After 24 hours | After 48 hours | After 72 hours |
| 293 cells | 2.68 | 3.67 | 3.81 |
| 293 cells with transferred pMazF-IZ | 6.88 | 15.46 | 14.2 |
| 293 cells with transferred pLuc-IZ | 129.44 | 450.35 | 583.94 |

TABLE 3

| | rRNA ratio (28 s/18 s) | | |
| --- | --- | --- | --- |
| | After 24 hours | After 48 hours | After 72 hours |
| 293 cells with transferred pMazF-IZ | 2.1 | 2.0 | 2.2 |
| 293 cells with transferred pLuc-IZ | 2.1 | 2.0 | 2.3 |

Example 9: Suppression of MazF Activity by MazE

A retrovirus vector plasmid pMSN-MazE which expresses MazE, which is the antitoxin for MazF, was constructed as follows.

pMT-MazE was constructed by inserting MazE gene (SEQ ID NO:24) between BamHI and XhoI sites in a vector pMT (Gene Therapy, 11:94-99 (2004)). A fragment containing SV40 promoter and neomycin phosphotransferase gene was obtained from pDON-AI by digestion with SalI and XhoI. The fragment was inserted into the XhoI site in pMT-MazE. The thus obtained MazE expression retrovirus vector plasmid was designated as pMSN-MazE.

G3T-hi cells (Takara Bio) were placed in a 6-cm plate containing DMEM supplemented with 10% fetal bovine serum (FBS). Transfection was carried out by a calcium phosphate method using 10 μg of the retrovirus vector plasmid pMSN-MazE and Retrovirus Packaging Kit Ampho (Takara Bio). The medium was exchanged for a fresh one 8 hours after initiation of transfection, and the cultivation was continued. The medium was exchanged again 24 hours after initiation of transfection. After 24 hours, the culture supernatant was collected and filtrated through a 0.45-μm filter, and the filtrate was used as a MSN-MazE virus supernatant. A 24-well non-tissue culture-treated plate was coated with RetroNectin (Takara Bio) according to the protocol. 0.5 ml of the MSN-MazE virus vector was added to the well. The plate was centrifuged at 32° C. at 2000×g for 2 hours to adsorb the MazE expression retrovirus vector to the RetroNectin-coated plate. After the supernatant was removed, 1 ml of a 293 cell suspension at 1×10$^5$ cells/ml was added to the well for infection. After the plate was incubated at 37° C. in the presence of 5% $CO_2$ for 24 hours, cells having a transferred gene were cultured in a medium containing geneticin (G418) at 0.5 mg/ml for two weeks to produce a polyclonal cell line 293-MazE which constitutively expresses MazE.

A retrovirus vector plasmid pSINH-HLTR-MazF was constructed by eliminating the neomycin phosphotransferase gene from pSIN-HLTR-MazF as described in Example 4 and inserting a hygromycin resistance gene in place of the gene.

G3T-hi cells (Takara Bio) were placed in a 6-cm plate containing DMEM supplemented with 10% fetal bovine serum (FBS). Transfection was carried out by a calcium phosphate method using 10 μg of the retrovirus vector plasmid pSINH-HLTR-MazF and Retrovirus Packaging Kit Ampho (Takara Bio). The medium was exchanged for a fresh one 8 hours after initiation of transfection, and the cultivation was continued. The medium was exchanged again 24 hours after initiation of transfection. After 24 hours, the culture supernatant was collected and filtrated through a 0.45-μm filter, and the filtrate was used as a SINH-HLTR-MazF virus supernatant. A 24-well non-tissue culture-treated plate was coated with RetroNectin (Takara Bio) according to the protocol. 0.5 ml of the SINH-HLTR-MazF virus vector was added to the well. The plate was centrifuged at 32° C. at 2000×g for 2 hours to adsorb the MazF expression retrovirus vector to the RetroNectin-coated plate. After the supernatant was removed, 1 ml of a suspension of 293-MazE cells or 293 cells at 1×10$^5$ cells/ml was added to the well for infection. After the plate was incubated at 37° C. in the presence of 5% $CO_2$ for 24 hours, cells having a transferred gene were cultured in a medium containing hygromycin B at 0.2 mg/ml for two weeks to produce polyclonal cell lines 293-MazE-MazF and 293-MazF.

A 24-well non-tissue culture-treated plate was coated with RetroNectin (Takara Bio) according to the protocol. 0.5 ml of the Tat expression retrovirus vector produced in Example 8 was added to the well. The plate was centrifuged at 32° C. at 2000×g for 2 hours to adsorb the retrovirus vector to the RetroNectin-coated plate. After the supernatant was removed, 1 ml of a suspension of cells of the cell line 293-MazE-MazF or 293-MazF at 1×10$^5$ cells/ml was added to the well for infection. 293 cells were also subjected to infection as a control. Cell growth was observed under microscope two days after infection. Growth of the 293-MazF cell was suppressed due to the expression of MazF by the action of the Tat protein. As to the 293-MazE-MazF cell, the action of MazF was neutralized by MazE and the growth was equivalent to the 293 cell. Thus, it was shown that MazE act as an antitoxin for MazF also in eukaryotes.

INDUSTRIAL APPLICABILITY

The present invention provides a nucleic acid construct that is effective in treatment and prevention of human immunodeficiency virus (HIV) infection. Since replication of HIV can be suppressed in a cell into which the nucleic acid construct is transferred, it is effective in treatment and prevention of HIV infection.

SEQUENCE LISTING FREE TEXT

SEQ ID NO:3; Synthetic DNA encoding MazF.
SEQ ID NO:4; Primer 5' HIV1 U3 to amplify a portion of HIV LTR.
SEQ ID NO:5; Primer 3' HIV1 R to amplify a portion of HIV LTR.
SEQ ID NO:6; Primer 3' HIV1 TAR to amplify a portion of HIV LTR.
SEQ ID NO:7; Primer 5' MazF to amplify a DNA encoding MazF.

SEQ ID NO:8; Primer 3' MazF to amplify a DNA encoding MazF.
SEQ ID NO:9; Primer 5' KpnI to amplify a DNA encoding GaLV envelope.
SEQ ID NO:10; Primer 3' ClaI to amplify a DNA encoding GaLV envelope.
SEQ ID NO:11; Primer NE1181-F to amplify a DNA encoding NE1181 polypeptide.
SEQ ID NO:12; Primer NE1181-R to amplify a DNA encoding NE1181 polypeptide.
SEQ ID NO:15; Synthetic DNA encoding NE1181 polypeptide.
SEQ ID NO:16; Primer DR0662-F to amplify a DNA encoding DR0662 polypeptide.
SEQ ID NO:17; Primer DR0662-R to amplify a DNA encoding DR0662 polypeptide.
SEQ ID NO:20; Primer to amplify a DNA encoding DR0662 polypeptide.
SEQ ID NO:21; Primer to amplify a DNA encoding DR0662 polypeptide.
SEQ ID NO:22; Primer to amplify a DNA encoding MazF.
SEQ ID NO:23; Primer to amplify a DNA encoding MazF.

The invention claimed is:

1. An isolated cell comprising a nucleic acid comprising a long terminal repeat (LTR) of human immunodeficiency virus (HIV) with which transcription is induced by Tat protein and/or Rev protein of human immunodeficiency virus; and a gene comprising the nucleotide sequence as set forth in SEQ ID NO: 3 encoding a naturally occurring *E. coli* MazF protein, which specifically cleaves a sequence 5'-A/CA-3' in a single-stranded RNA, wherein the gene is placed downstream of said LTR such that its expression can be controlled by said LTR.

2. The isolated cell of claim 1, wherein the cells is a T cell or a T cell precursor.

3. A method for producing the cell of claim 1, the method comprising the step of introducing a nucleic acid into an isolated cell, wherein the nucleic acid comprises a long terminal repeat (LTR) of human immunodeficiency virus (HIV) with which transcription is induced by Tat protein and/or Rev protein of human immunodeficiency virus; and a gene comprising the nucleotide sequence as set forth in SEQ ID NO: 3 encoding a naturally occurring *E. coli* MazF protein, which specifically cleaves a sequence 5'-A/CA-3' in a single-stranded RNA, wherein the gene is placed downstream of said LTR such that its expression can be controlled by said LTR.

4. The method of claim 3, wherein the nucleic acid is incorporated into a virus vector.

5. The method of claim 4, wherein the nucleic acid is incorporated into a retrovirus vector.

6. The method of claim 3, wherein the cell is a T cell or a T cell precursor.

* * * * *